(12) United States Patent
O'Dell et al.

(10) Patent No.: US 7,754,841 B2
(45) Date of Patent: Jul. 13, 2010

(54) POLYMER

(75) Inventors: Richard O'Dell, Taufkirchen (DE); Thomas Pounds, Cambridge (GB); Paul Wallace, Hertfordshire (GB); Carl Towns, Essex (GB); Mary Mc Kiernan, Cambridgeshire (GB)

(73) Assignee: Merck Patent GmbH, Darmstadt (DE)

( * ) Notice: Subject to any disclaimer, the term of this patent is extended or adjusted under 35 U.S.C. 154(b) by 187 days.

(21) Appl. No.: 10/560,861

(22) PCT Filed: Jun. 22, 2004

(86) PCT No.: PCT/EP2004/006721

§ 371 (c)(1), (2), (4) Date: Mar. 7, 2006

(87) PCT Pub. No.: WO2004/113412

PCT Pub. Date: Dec. 29, 2004

(65) Prior Publication Data

US 2006/0149016 A1 Jul. 6, 2006

(30) Foreign Application Priority Data

Jun. 23, 2003 (EP) .................................. 03014042

(51) Int. Cl.
*C08G 79/08* (2006.01)
(52) U.S. Cl. ........................... 528/8; 528/394; 570/129; 570/183; 257/40
(58) Field of Classification Search .................. 528/394, 528/8; 570/129, 183; 257/40
See application file for complete search history.

(56) References Cited

U.S. PATENT DOCUMENTS

| | | | |
|---|---|---|---|
| 4,539,507 A | 9/1985 | VanSlyke et al. | |
| 5,621,131 A | 4/1997 | Kreuder et al. | |
| 5,723,873 A | 3/1998 | Yang | |
| 5,777,070 A * | 7/1998 | Inbasekaran et al. | 528/394 |
| 5,798,170 A | 8/1998 | Zhang et al. | |
| 6,653,438 B1 | 11/2003 | Spreitzer et al. | |
| 6,956,095 B2 | 10/2005 | Treacher et al. | |
| 2004/0260090 A1 | 12/2004 | Treacher et al. | |
| 2005/0263758 A1 | 12/2005 | Treacher et al. | |

FOREIGN PATENT DOCUMENTS

| | | |
|---|---|---|
| EP | 0 707 020 | 4/1996 |
| EP | 0 842 208 | 5/1998 |
| EP | 0 851 714 | 7/1998 |
| EP | 0 880 303 | 11/1998 |
| EP | 0 901 176 | 3/1999 |
| EP | 0 947 123 | 10/1999 |
| EP | 0 949 850 | 10/1999 |
| GB | 2 348 316 | 9/2000 |
| WO | WO-90/13148 | 11/1990 |
| WO | WO-98/10621 | 3/1998 |
| WO | WO-99/48160 | 9/1999 |
| WO | WO-00/22026 | 4/2000 |
| WO | WO-00/48258 | 8/2000 |
| WO | WO-00/53656 | 9/2000 |
| WO | WO-00/55927 | 9/2000 |
| WO | WO-01/19142 | 3/2001 |
| WO | WO-01/66618 | 9/2001 |
| WO | WO-01/81649 | 11/2001 |
| WO | WO-02/26859 | 4/2002 |
| WO | WO-03/48225 | 6/2003 |
| WO | WO-2004/022626 | 3/2004 |

OTHER PUBLICATIONS

Setayesh et al Bridging the Gap between Polyfluorene and Ladder-Poly-p-phenylene:Synthesis and Characterization of Poly-2,8-indenofluorene, Macromolecules, 2000, 33, 2016-2020.*
Reisch Dissertation, Oligo- und Poly(indenofluorene) . . . , Mainz, 2000, pp. 27 and 115.*
Kim Assemblies of conjugated polymers. Intermolecular and intramolecular effects on the photophysical properties of conjugated polymers, Pure Appl. Chem., vol. 74, No. 11, pp. 2031-2044, 2002.*

* cited by examiner

*Primary Examiner*—James Seidleck
*Assistant Examiner*—Gregory Listvoyb
(74) *Attorney, Agent, or Firm*—Connolly Bove Lodge & Hutz LLP

(57) ABSTRACT

The present invention relates to new semiconductive oligomers and polymers, a process for their manufacture and their use in thin film electronic and optical devices, such as organic light emitting diodes (OLED) and photovoltaic devices, eg. solar cells and photodetectors.

18 Claims, No Drawings

US 7,754,841 B2

POLYMER

RELATED APPLICATIONS

This application is a national stage application (under 35 U.S.C. 371) of PCT/EP2004/006721 filed Jun. 22, 2004 which claims benefit to European application 03014042.0 filed Jun. 23, 2003.

FIELD OF THE INVENTION

This invention relates to semiconductive oligomers and polymers, their synthesis and use in thin film electronic and optical devices.

BACKGROUND OF THE INVENTION

Semiconducting organic materials are attracting a great deal of interest due to their processability and the broad spectrum of optical and electronic properties that may be selected according to the structure of the organic material.

One application of such materials is in switching devices, in particular as organic field effect transistors as described in, for example, Adv. Mater. 1998 10(5), 365-377.

Another application is in opto-electrical devices using a semiconducting organic material for light emission (an organic light emitting device or "OLED") or as the active component of a photocell or photodetector (a "photovoltaic" device). The basic structure of these devices is a semiconducting organic layer sandwiched between a cathode for injecting or accepting negative charge carriers (electrons) and an anode for injecting or accepting positive charge carriers (holes) into the organic layer.

In an organic electroluminescent device, electrons and holes are injected into a layer of electroluminescent semiconducting material where they combine to generate excitons that undergo radiative decay. Holes are injected from the anode into the highest occupied molecular orbital (HOMO) of the electroluminescent material; electrons are injected from the cathode into the lowest unoccupied molecular orbital (LUMO) of the electroluminescent material. In WO 90/13148 the organic light-emissive material is a polymer, namely poly(p-phenylenevinylene) ("PPV"). This class of device is commonly known as a polymer light emitting device (PLED). In U.S. Pat. No. 4,539,507 the organic light-emissive material is of the class known as small molecule materials, such as (8-hydroxyquinoline) aluminium ("Alq$_3$").

One alternative to PPVs are 2,7-linked polyfluorenes as disclosed in EP 0842208 which have attracted attention because of their advantage of solution processability, such as suitability for inkjet printing. Furthermore, fluorene monomers with appropriate leaving groups are amenable to Suzuki or Yamamoto polymerisation. Suzuki polymerisation in particular affords a great deal of control over the regioregularity and therefore the properties of the polymer. Fluorene repeat units may therefore be used as a "building block" in creating co-polymers with a wide range of charge transporting and/or emissive properties.

However, there are a number of disadvantages associated with polyfluorenes which have led to a search for alternative electron transporting and light emitting units. These disadvantages include the tendency of polyfluorenes to aggregate and the fact that when blue light emission occurs from fluorene based polymers the emission does not occur in the region of the electromagnetic spectrum in which the human eye is most sensitive.

One alternative to fluorene repeat units are trans-indenofluorene repeat units (illustrated below) as disclosed in, for example, Macromolecules 2000, 33(6), 2016-2020 and Advanced Materials, 2001, 13, 1096-1099.

Polymers comprising the tetraoctyl trans-indenofluorene unit are described as having

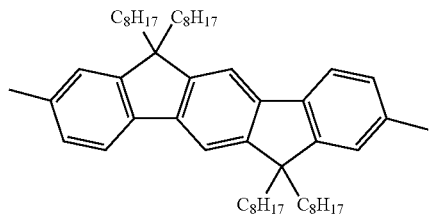

a bathochromically shifted emission wavelength which leads to a blue emission colour matched to the sensitivity of the human eye. However, poly(trans-indenofluorenes) have a lower conductivity than corresponding polyfluorenes.

It is therefore an object of the invention to provide a repeat unit that possesses the advantages of trans-indenofluorene over fluorene without suffering from loss of conduction.

SUMMARY OF THE INVENTION

The present inventors have surprisingly found that oligomers or polymers comprising cis-indenofluorene repeat units have comparable or better conduction than corresponding oligomers or polymers comprising fluorene repeat units. Furthermore, the present inventors have surprisingly found that oligomers or polymers comprising cis-indenofluorene repeat units are blue-shifted relative to the corresponding oligomers or polymers comprising trans-indenofluorene repeat units.

Accordingly, in a first aspect the invention provides an oligomer or polymer comprising an optionally substituted first repeat unit of formula (Ir):

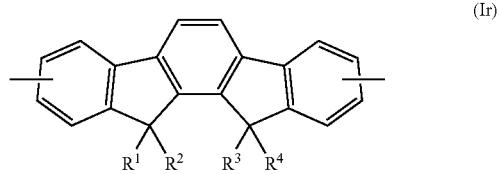

wherein $R^1$, $R^2$, $R^3$ and $R^4$, which may be the same or different, are independently selected from hydrogen or a substituent and two or more of $R^1$, $R^2$, $R^3$ and $R^4$ may be linked to form a ring.

Without wishing to be bound by any theory, it is believed that locating groups $R^1$, $R^2$, $R^3$ and $R^4$ on the same side of the repeat unit backbone enables close packing of oligomers or polymers containing the backbone, leading to improved conductivity, as compared to trans-indenofluorene repeat units which have two substituent groups on one side of the repeat unit and two substituent groups on the opposite side of the backbone. Furthermore, the present inventors have found that there is a small twist within the repeat unit of formula (Ir) which is believed to be due to steric interactions between groups $R^1$ and $R^2$ and groups $R^3$ and $R^4$. This twist, which is not present in the corresponding trans-indenofluorene repeat unit; renders the cis-indenofluorene unit of formula (Ir) less prone to aggregation than a corresponding trans-indenofluorene unit. Finally, this twist also blue-shifts the colour of emission of oligomers or polymers comprising the repeat unit of formula (I) as compared to oligomers or polymers comprising repeat units of trans-indenofluorenes.

Certain substituents $R^1$, $R^2$, $R^3$ and $R^4$ may modify the properties of the repeat unit, and therefore the polymer, such as its solubility, electron affinity or glass transition temperature (Tg). Therefore, it is preferred that each $R^1$, $R^2$, $R^3$ and $R^4$ is independently selected from the group consisting of optionally substituted alkyl, alkoxy, aryl, or heteroaryl. More preferably, at least one of $R^1$, $R^2$, $R^3$ and $R^4$ is optionally substituted phenyl or optionally substituted $C_{1-20}$ alkyl.

Particularly preferred substituents are $C_{1-20}$ alkyl or alkoxy, in particular branched alkyl or n-alkyl, such as n-octyl, as solubilising substituents; optionally substituted phenyl or oligophenyl (e.g. biphenyl or terphenyl) as Tg increasing substituents, in particular unsubstituted phenyl, phenyl substituted with alkyl or alkoxy to improve solubility and phenyl substituted with fluorine, fluoroalkyl, perfluoroalkyl to increase electron affinity; and optionally substituted, electron deficient heteroaryls in particular pyridine, pyrimidine and triazine, each of which may be unsubstituted or substituted with substituents listed as for phenyl above.

Asymmetry within the polymer may be desirable in order to minimise the possibility of aggregation. Therefore, it is preferred that at least one of $R^1$, $R^2$, $R^3$ and $R^4$ is different from at least one other of $R^1$, $R^2$, $R^3$ and $R^4$. In one particularly preferred embodiment, $R^1$ and $R^2$ are both optionally substituted alkyl and $R^3$ and $R^4$ are both optionally substituted aryl. In another particularly preferred embodiment, $R^1$ and $R^3$ are both optionally substituted alkyl and $R^2$ and $R^4$ are both optionally substituted aryl.

Appropriate selection of the four substituents $R^1$, $R^2$, $R^3$ and $R^4$ enables greater control over the properties of the oligomer or polymer as compared to corresponding fluorenes wherein there are only two such substitution positions. Further modification of the properties of the repeat unit of the invention may be achieved by substitution of one or more of the phenyl groups of the repeat unit of formula (Ir). Preferably, such substitution takes the form of a repeat unit of formula (II):

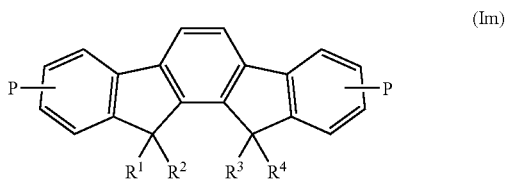

(II)

wherein at least one of $R^7$ and $R^8$ represents a substituent, and $R^7$ and $R^8$ together may form a ring.

In one preferred embodiment, $R^7$ and $R^8$ are both substituents and are the same or different. Preferred substituents $R^7$ and $R^8$ are optionally substituted alkyl, alkoxy, aryl, or heteroaryl; particularly preferred substituents $R^7$ and $R^8$ are as described above with reference to $R^1$, $R^2$, $R^3$ and $R^4$.

Preferably, the first repeat unit is linked through the 2- and 9-positions as shown below (because this maximises conjugation through the repeat unit).

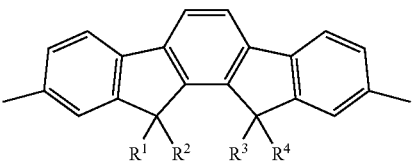

The polymer, according to the invention may be a homopolymer or a co-polymer. Where the polymer is a co-polymer wide range of properties may be accessed by appropriate selection of co-repeat unit or co-repeat units. Therefore, the oligomer or polymer preferably comprises a second repeat unit. Preferably, the second repeat unit comprises an aryl group that is directly conjugated to the first repeat unit. More preferably, the second repeat unit is selected from optionally substituted aryl, heteroaryl and triarylamine repeat units.

In a second aspect, the invention provides an optionally substituted monomer of formula (Im):

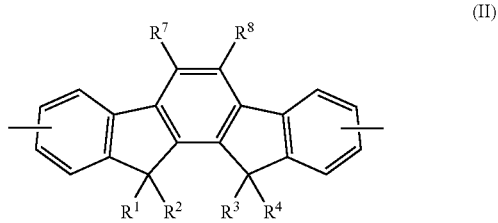

(Im)

wherein $R^1$, $R^2$, $R^3$ and $R^4$, which may be the same or different, are independently selected from hydrogen or a substituent and two or more of $R^1$, $R^2$, $R^3$ and $R^4$ may be linked to form a ring; and each P represents a polymerisable group.

Advantageous polymerisation techniques include Suzuki and Yamamoto polymerisations which operate via a "metal insertion" wherein the metal atom of a metal complex catalyst is inserted between an aryl group and a leaving group of a monomer. Therefore, each P preferably represents a leaving group capable of participating in a polycondensation mediated by a metal of variable oxidation state.

Preferably, the polycondensation is mediated by a metal insertion.

Preferably, each P is independently selected from halogen; a moiety of formula $—O—SO_2—Z$ wherein Z is selected from the group consisting of optionally substituted alkyl and aryl; or a reactive boron group selected from a boronic acid, a boronic ester or a borane. Preferred halogens are bromine, chlorine and iodine, more preferably bromine.

In a third aspect, the invention provides a process for preparing an oligomer or polymer comprising the step of oligomerising or polymerising a monomer according to the second aspect of the invention.

In a first preferred embodiment of the third aspect, each P is independently a halogen or a moiety of formula $—O—SO_2—Z$, wherein Z is selected from the group consisting of optionally substituted alkyl and aryl, and the monomer of formula (III) is oligomerised or polymerised in the presence of a nickel complex catalyst.

In a second preferred embodiment of the third aspect, the monomer of formula (III) is oligomerised or polymerised with a second aromatic monomer in the presence of a palladium complex catalyst and a base and (a) each P is the same or different and comprises a reactive boronic group and the second monomer comprises two reactive groups independently selected from halogen and a moiety of formula —O—SO$_2$—Z, or (b) each P independently comprises a halogen or a moiety of formula —O—SO$_2$—Z and the second monomer comprises two reactive boron groups which are the same or different.

In a third preferred embodiment of the third aspect, one P is a reactive boron group and the other P is a halogen or a moiety of formula —O—SO$_2$—Z.

In a fourth aspect, the invention provides an optical device comprising an oligomer or polymer according to the first aspect of the invention. Preferably, the oligomer or polymer is located between a first electrode for injection of charge carriers of a first type and a second electrode for injection of charge carriers of a second type.

In addition to their applicability in optical devices such as OLEDs or photovoltaic devices, the oligomers or polymers according to the invention may be used in a switching device. Accordingly, in a fifth aspect the invention provides a switching device comprising an oligomer or polymer according to the first aspect of the invention. In a preferred embodiment, this aspect of the invention provides a field effect transistor comprising an insulator having a first side and a second side; a gate electrode located on the first side of the insulator; an oligomer or polymer according to the first aspect of the invention located on the second side of the insulator; and a drain electrode and a source electrode located on the oligomer or polymer.

In a sixth aspect, the invention provides an integrated circuit comprising a field effect transistor according to the fifth aspect of the invention.

In a seventh aspect, the invention provides A method of forming an optionally substituted compound of formula (I):

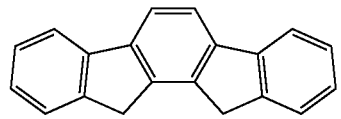

(I)

comprising the step of eliminating LG-H from an optionally substituted compound of formula (Ip):

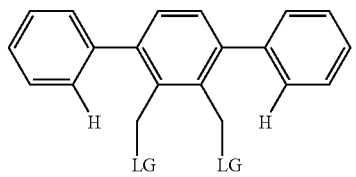

(Ip)

wherein each LG is the same or different and represents a leaving group.

Suitable leaving groups include halide, —OR, —SR, —OSO$_2$R and —NR$_2$ wherein each R independently represents hydrogen or optionally substituted alkyl or aryl. Preferably, each LG is hydroxy.

Preferably, the elimination is performed in the presence of an acid.

Preferably, the acid is polyphosphoric acid.

Preferably, the method comprises the further step of providing a polymerisable group P on each of the outer phenyl rings of the compound of formula (I) or (Ip).

DETAILED DESCRIPTION OF THE INVENTION

Oligomers and polymers according to the invention may be used as solution processable, electron transporting, hole transporting and/or emissive materials in organic light emitting devices. The invention is described hereinafter with reference to polymers, however it will be appreciated that features described herein may apply equally to oligomers.

The polymers may be prepared by Suzuki polymerisation as described in, for example, WO 00/53656 or WO 03/048225 and Yamamoto polymerisation as described in, for example, T. Yamamoto, "Electrically Conducting And Thermally Stable π-Conjugated Polyarylenes Prepared by Organometallic Processes", Progress in Polymer Science 1993, 17, 1153-1205 or WO 04/022626. For example, in the synthesis of a linear polymer by Yamamoto polymerisation, a monomer having two reactive halide groups P is used. Similarly, according to the method of Suzuki polymerisation, at least one reactive group P is a reactive boron group.

Suzuki polymerisation employs a Pd(0) complex or a Pd(II) salt. Pd(0) complexes are preferred, in particular Pd(0) complexes bearing at least one phosphine ligand such as Pd(Ph$_3$P)$_4$. Suzuki polymerisation is performed in the presence of a base, for example sodium carbonate or an organic base such as tetraethylammonium carbonate.

Yamamoto polymerisation employs a Ni(0) complex, for example bis(1,5-cyclooctadienyl)nickel(0).

Suzuki polymerisation may be used to prepare regioregular, block and random copolymers. In particular, homopolymers or random copolymers may be prepared when one reactive group P is a halogen and the other reactive group P is a reactive boron group. Alternatively, block or regioregular, in particular AB, copolymers may be prepared when both reactive groups of a first monomer are boron and both reactive groups of a second monomer are halide.

The monomer according to the invention may be polymerised alone to form a homopolymer or in the presence of one or more co-monomers to form a co-polymer. Possible co-repeat units derived from such co-monomers are outlined below; it will be appreciated that each of these co-repeat units may be derived from a comonomer comprising two polymerisable groups independently selected from halogen (preferably chlorine, bromine or iodine, more preferably bromine), a boronic acid group, a boronic ester group and a borane group.

As alternatives to halogens as described above, leaving groups such as tosylate, mesylate and triflate may also be used.

Where the polymer according to the invention is a co-polymer, one class of co-repeat units is arylene repeat units, in particular: 1,4-phenylene repeat units as disclosed in J. Appl. Phys. 1996, 79, 934; fluorene repeat units as disclosed in EP 0842208, trans-indenofluorene repeat units as disclosed in, for example, Macromolecules 2000, 33(6), 2016-2020 and spirobifluorene repeat units as disclosed in, for example EP 0707020. Each of these repeat units is optionally substituted. Examples of substituents include solubilising groups such as $C_{1-20}$ alkyl or alkoxy; electron withdrawing groups such as fluorine, nitro or cyano; and substituents for increasing glass transition temperature (Tg) of the polymer such as bulky groups, e.g. tert-butyl.

A further class of preferred co-repeat units are repeat units comprising one or two amino groups in the repeat unit backbone such as co-repeat units comprising triarylamine groups, in particular repeat units of formulae 1-6:

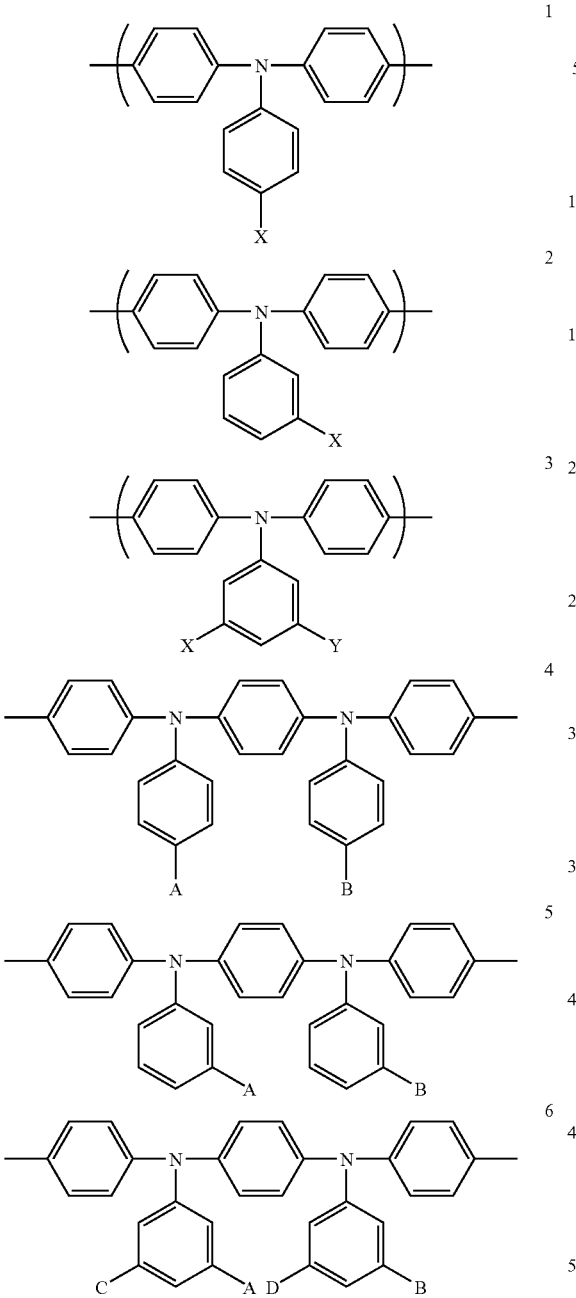

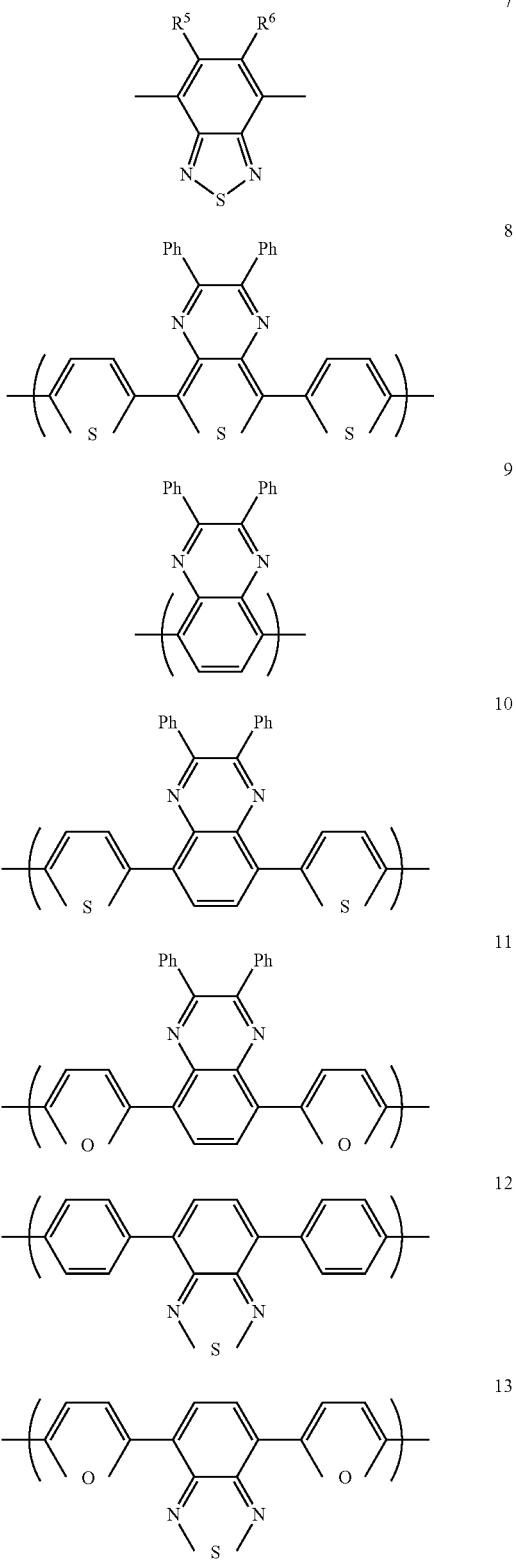

A yet further class of co-repeat units include heteroaryl repeat units such as optionally substituted 2,5-thienyl, pyridyl, diazine, triazine, azole, diazole, triazole, oxazole or oxadiazole; or optionally substituted units of formulae 7-19:

X and Y may be the same or different and are substituent groups. A, B, C and D may be the same or different and are substituent groups. It is preferred that one or more of X, Y, A, B, C and D is independently selected from the group consisting of alkyl, aryl, perfluoroalkyl, thioalkyl, cyano, alkoxy, heteroaryl, alkylaryl and arylalkyl groups. One or more of X, Y, A, B, C and D also may be hydrogen. It is preferred that one or more of X, Y, A, B, C and D is independently an unsubstituted, isobutyl group, an n-alkyl, an n-alkoxy or a trifluoromethyl group because they are suitable for helping to select the HOMO level and/or for improving solubility of the polymer.

Use of trifluoromethyl groups in repeat units of this type is disclosed in WO 01/66618.

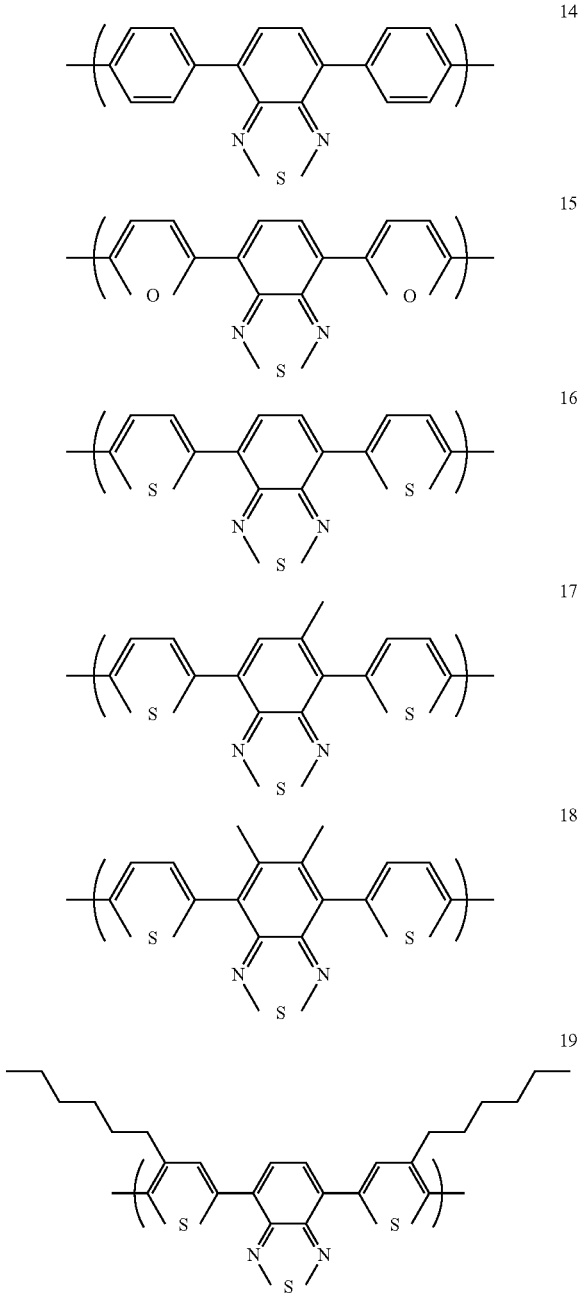

wherein $R^5$ and $R^6$ are the same or different and are each independently a substituent group. Preferably, one or more of $R^5$ or $R^6$ may be selected from hydrogen, alkyl, aryl, perfluoroalkyl, thioalkyl, cyano, alkoxy, heteroaryl, alkylaryl, or arylalkyl. These groups are preferred for the same reasons as discussed in relation to X, Y, A, B, C and D above. Preferably, for practical reasons, $R^5$ and $R^6$ are the same.

When used in an OLED, polymers according to the invention possess at least one of hole transporting, electron transporting and emissive properties. Where the polymer has more than one of these properties, different properties may be provided by different segments of a block co-polymer, in particular segments of the polymer backbone as described in WO 00/55927 or pendant groups as described in WO 02/26859.

Alternatively, if the polymer of the invention has only one or two of the properties of hole transport, electron transport and emission, it may be blended with one or more further polymers having the remaining required property or properties as described in WO 99/48160.

Polymers according to the invention may be used as active materials in any of the aforementioned optical devices, in particular electroluminescent devices and photovoltaic devices (i.e. photodetectors or photocells). Such optical devices comprise a substrate carrying the polymer located between a positive charge carrying electrode and a negative charge carrying electrode. In forming these devices, the polymer may be deposited from solution by any one of a range of techniques including in particular techniques such as spin-coating, dip-coating, inkjet printing as disclosed in EP 0880303, laser transfer as described in EP 0851714, flexographic printing, screen printing and doctor blade coating.

Optical devices tend to be sensitive to moisture and oxygen. Accordingly, the substrate of the device preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

Although not essential, the presence of a layer of organic hole injection material over the anode is desirable as it assists hole injection from the anode into the layer or layers of semiconducting polymer. Examples of organic hole injection materials include PEDT/PSS as disclosed in EP 0901176 and EP 0947123, or polyaniline as disclosed in U.S. Pat. No. 5,723,873 and 5,798,170.

The cathode is selected in order that electrons are efficiently injected into the device and as such may comprise a single conductive material such as a layer of aluminium. Alternatively, it may comprise a plurality of metals, for example a bilayer of calcium and aluminium as disclosed in WO 98/10621, or a thin layer of dielectric material such as lithium fluoride to assist electron injection as disclosed in, for example, WO 00/48258.

The device is preferably encapsulated with an encapsulant to prevent ingress of moisture and oxygen. Suitable encapsulants include a sheet of glass, films having suitable barrier properties such as alternating stacks of polymer and dielectric as disclosed in, for example, WO 01/81649 or an airtight container as disclosed in, for example, WO 01/19142.

In a practical optoelectronic device, at least one of the electrodes is semi-transparent in order that light may be absorbed (in the case of a photoresponsive device) or emitted (in the case of a PLED). Where the anode is transparent, it typically comprises indium tin oxide. Examples of transparent cathodes are disclosed in, for example, GB 2348316. Where the polymer of the invention is used in a switching device such as a field effect transistor, it will be appreciated that all of the electrodes may be opaque.

The PLED may be a passive matrix or active matrix device.

EXAMPLES

Monomer Example

A monomer according to the invention was prepared in accordance with the scheme set out below:

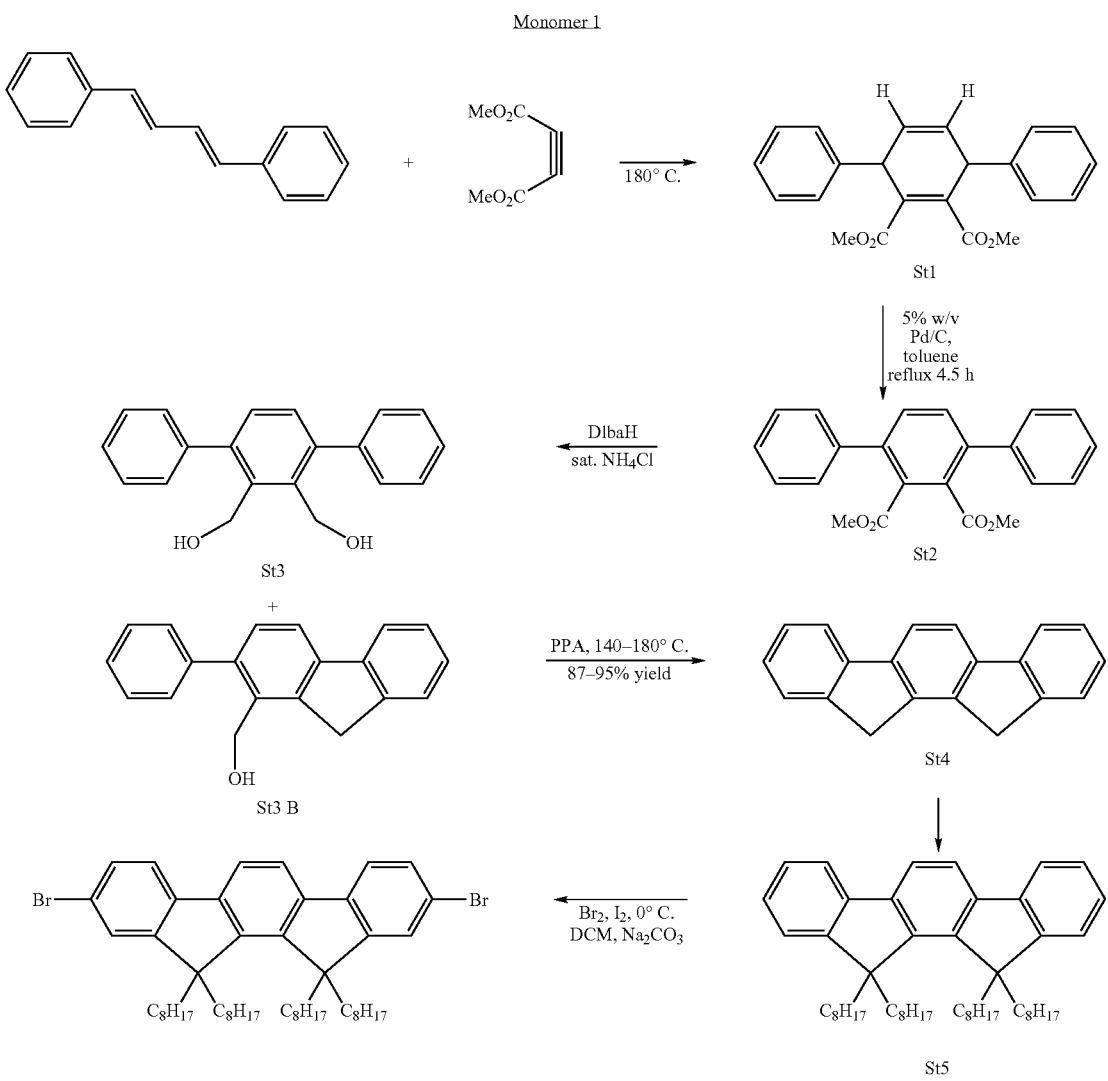

Synthesis of Diene, St1

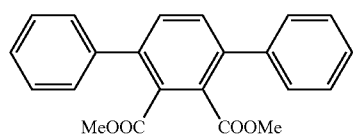

1,4-Diphenyl-1,3-butadiene (500 g, 2.42 moles) and dimethylacetylenedicarboxylate (378 g, 2.66 moles) were charged to a 2 L vessel. Toluene (750 ml) was added and the mixture heated to reflux (oil bath temperature 145° C., diene dissolved >90° C.). The reaction was refluxed for 20 h (overnight) before being cooled to room temperature. Evaporation of the toluene afforded a yellow/brown solid, which was recrystallised from 2-propanol to give 780 g, 92.5% yield of the desired product as a white solid. GC-MS gave a single peak m/z 348, HPLC 99.3%; $^1$H NMR 3.54 (6H, s, 2×CH$_3$), 4.47 (2H, s), 5.77 (2H, S), 7.24-7.34 (10H, m).

Synthesis of Terphenyl Cis-dimethylester, St2

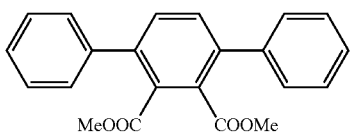

To a toluene (100 ml) solution of the diene (stage 1 product, 10 g, 28.7 mmol) was added palladium 10 wt. % on activated carbon (1.5 g, 10% wt). The reaction was refluxed (oil bath 130° C.) for 20 h (overnight). The reaction was cooled slightly (80° C.) and diluted with toluene (100 ml) before hot filtering through a pad of celite filter agent. The filter cake was washed with a further 500 ml hot toluene to remove all of the product. Cooling of the filtrate crystallised the desired product as a white solid 7.75 g, 78%. GC-MS≧95%, m/z 346; $^1$H NMR 3.62 (6H, s, 2×CH$_3$), 7.36-7.45 (10H, m), 7.52 (2H, s).

Synthesis of Terphenyl Cis diol, St3, St3B

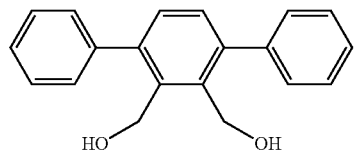

A solution of diester (10 g, 17.56 mmol) in dichloromethane (130 mL) was added dropwise over 1 hour into a solution of diisobutyl aluminiumhydride (1 M in hexane). After 2 h of stirring at room temperature the reaction was quenched, pouring the reaction mixture into a saturated solution of ammonium chloride. The desired product was extracted into dichloromethane (20 mL MeOH added). The organic layer was dried (MgSO$_4$) and evaporated under vacuum affording 6.45 g (77% yield) of desired product. GC-MS confirmed 90% conversion to the diol and 10% of starting material remaining. $^1$H NMR 2.925 (2H, OH), 4.78 (4H, s, CH$_2$OH), 7.34-7.46 (12H).

Synthesis of Cis indenofluorene, St5

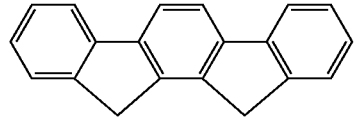

The white dibenzylic alcohol (2.65 g, 9.1 mmol) was added to polyphosphoric acid (12 g) and heated to 180° C. Once at temperature the PPA became liquid and the white powder turned yellow. The reaction mixture was cooled to room temperature and then treated with a 10% solution of NaOH. 2.213 g (95% yield) of cis indenofluorene precipitated out as a grey/white solid; GC-MS indicated 98% of desired material and 2% of mono cyclised (St3B); $^1$H NMR 3.95 (4H, S, CH$_2$×2), 7.31 (2H, t, J 7.2), 7.39 (2H, t,-J 7.2), 7.59 (2H, d, J 8.0), 7.82 (2H, s), 7.83 (2H, d, J 7.2); $^{13}$C NMR 35.738, 118.954, 120.167, 125.374, 126.746, 127.089, 139.593, 141.057, 142.307, 143.306.

Synthesis of St5

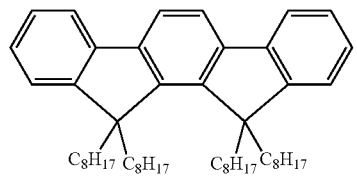

To a cooled (−78° C.) solution of cis indenofluorene (2 g, 7.9 mmol) in THF (120 mL) was added BuLi (2.5M, 17.38 mmol). After addition was complete, the reaction mixture was left to stir at −78° C. for a further 2 h and then left to warm to room temperature. The reaction mixture was then re-cooled to −78° C. and octyl bromide (3.26 mL, 18.96 mmol) added. The reaction mixture was allowed to room temperature over night and the whole lithiation and alkylation process repeated. The reaction was poured onto a mixture of petroleum ether-Et$_2$O and washed with H$_2$O. The organic layer was isolated, dried (MgSO$_4$) and the excess octyl bromide/octane removed using Kugel distillation (40° C., 10$^{-2}$ mbar). GC-MS indicated 81% dialkyl and 15% trialkylated product. The isolated mixed product (1.34 g) was put through the lithiation-alkylation procedure again. To afford the desired tetra-alkylated product the whole experimental procedure was repeated using a further 5.2 equivalents of BuLi and 6 equivalent of octyl bromide. 1.069 g of desired material was isolated and used crude in the next stage. $^1$H NMR 0.4-1.4 (30H), 2.2 (2H, td, J 4.4, 12.8), 2.4 (2H, td, J 4.4, 12.8), 7.26-7.33 (6H, m), 7.70 (2H, d, J 7.6), 7.74 (2H, s); $^{13}$C NMR 14.29, 22.84, 24.30, 29.68, 29.82, 30.32, 32.05, 40.88, 58.24, 119.05, 119.130, 121.78, 126.79, 127.24, 141.16, 142.30, 146.49, 150.98.

Synthesis of Monomer 1

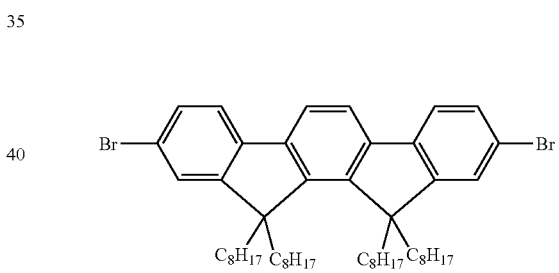

To a 0° C. solution of St5 (1.069 g), iodine (catalytic) in CH$_2$Cl$_2$ (25 mL) was added a solution of Na$_2$CO$_3$ (0.387 g) in H$_2$O (6 mL). After stirring for 5 minutes, bromine (183 μL) was added dropwise. The reaction mixture was left to stir overnight. The reaction was treated with a 10% sodium thiosulphate solution (20 mL). The organic layer was removed, washed with water (2×20 mL). The organic layer was separated from the aqueous, dried (MgSO$_4$Y and evaporated under vacuum. Column chromatography elute hexane gave 450 mg of mono and di brominated product; confirmed by GC-MS. This mixture was subjected again to bromination.

Indenofluorene repeat units carrying substituents on the central phenyl ring of the repeat unit were prepared in accordance with the following scheme:

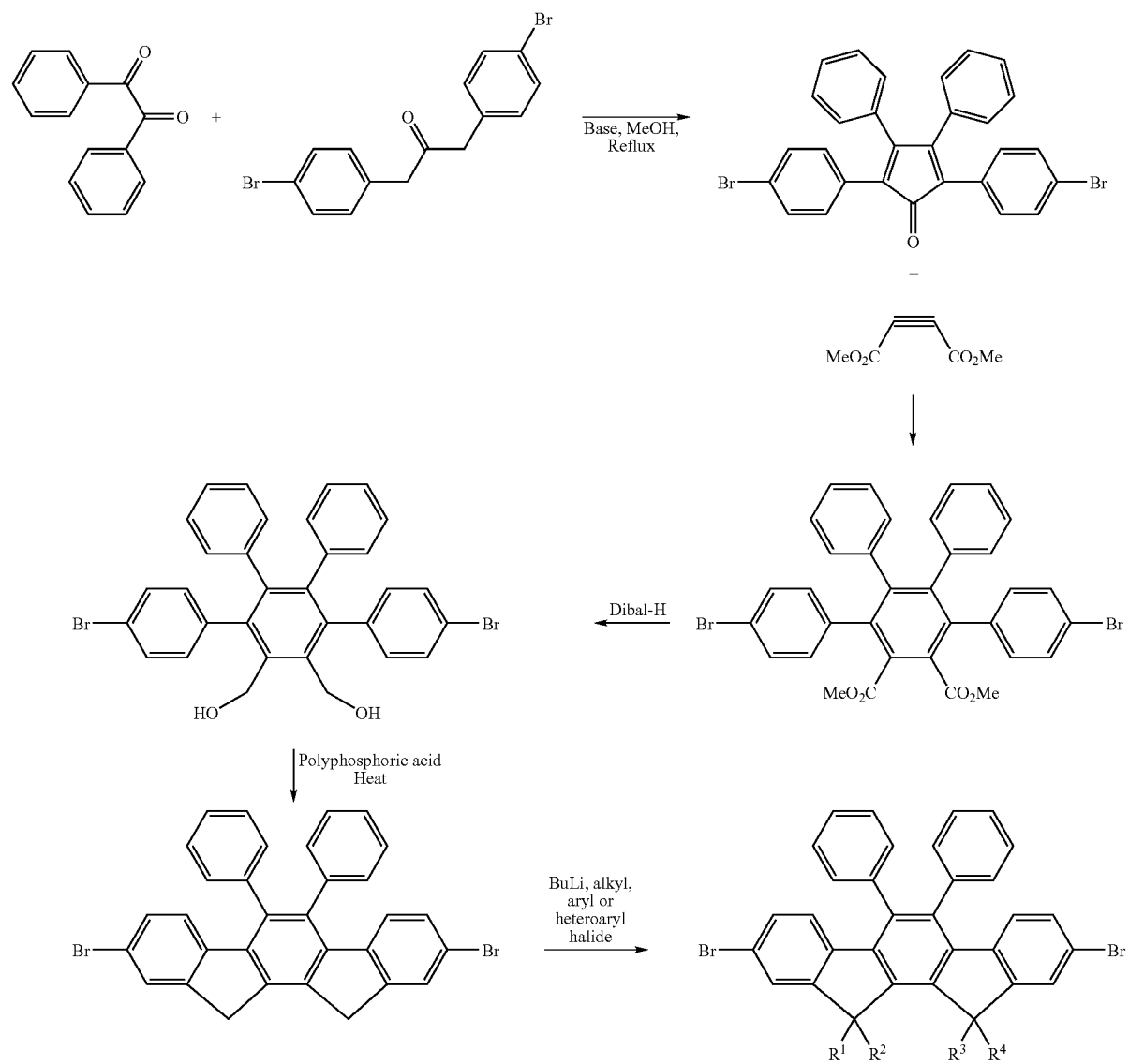
In addition to providing substituents on the central ring, the central ring of the monomer may comprise a fused ring, as illustrated below wherein the central ring is a benzothiadiaz-ole. The first step may be performed by Suzuki coupling of the starting dibromo compound with two equivalents of a phenyl boronic ester.
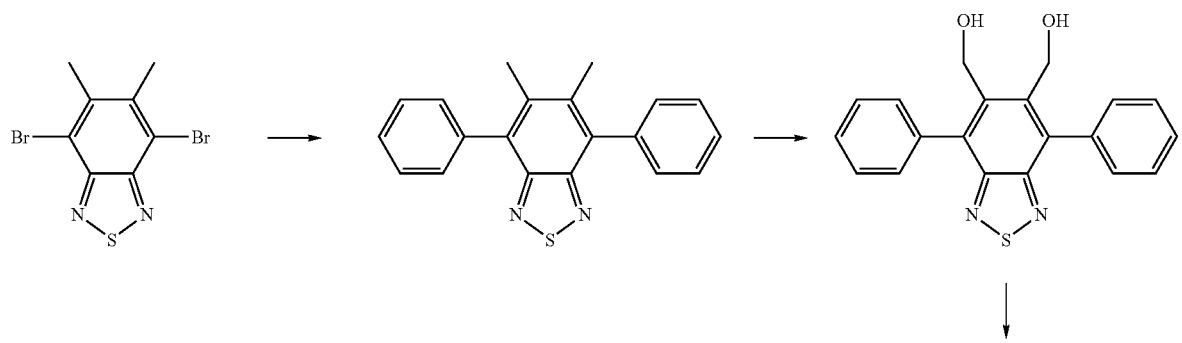

-continued

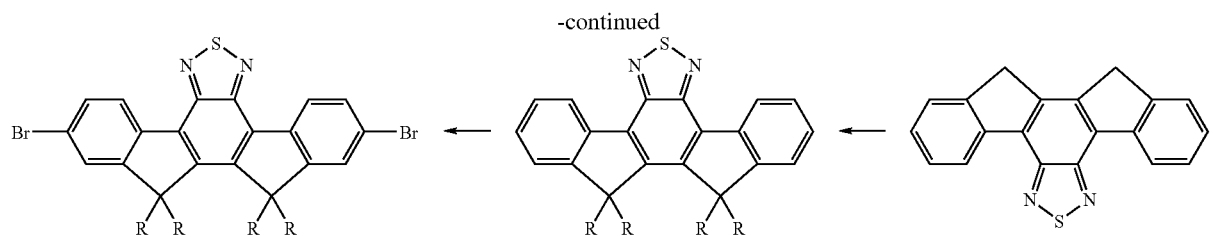

Finally, cis-indenofluorene monomers carrying different substituents $R^1$-$R^4$ were prepared in accordance with the following scheme. As shown in the scheme, asymmetric substitution at the 11 and 12 positions was accomplished by forming an amide as described in Weinreb, Tetrahedron Letters 22(39), 3815-3818, 1981; reacting the amide with one equivalent of a first alkyl, aryl or heteroaryl lithium to form a ketone; and reacting the ketone with one equivalent of a second alkyl, aryl or heteroaryl lithium that is different from the first alkyl, aryl or heteroaryl lithium.

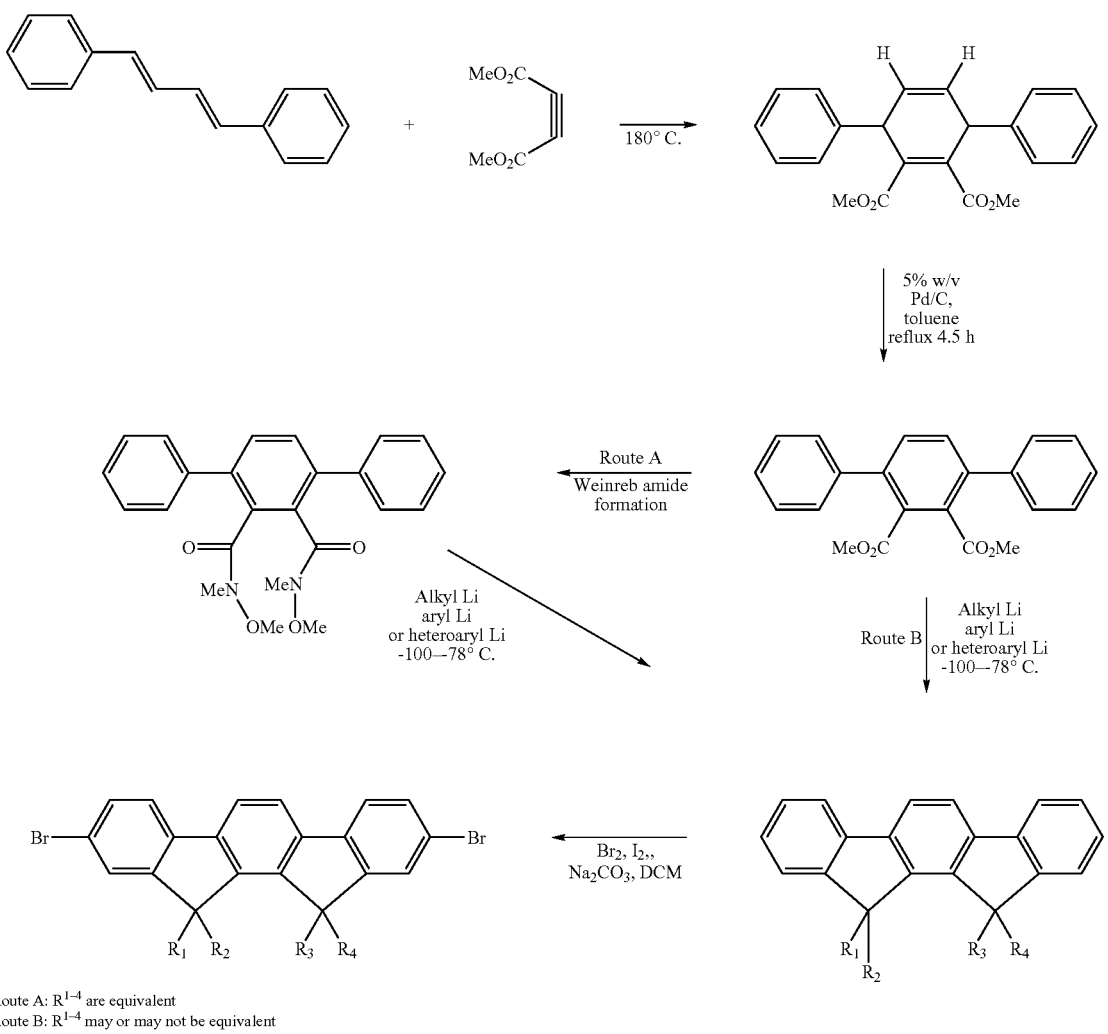

Route A: $R^{1-4}$ are equivalent
Route B: $R^{1-4}$ may or may not be equivalent

Polymer Examples

Polymers according to the invention were prepared in accordance with the method set forth in WO 00/53656 by polymerisation of the monomers shown below. Boronic esters were derived from Monomer 1 in accordance with the method set forth in WO 00/53656.

Polymer 1
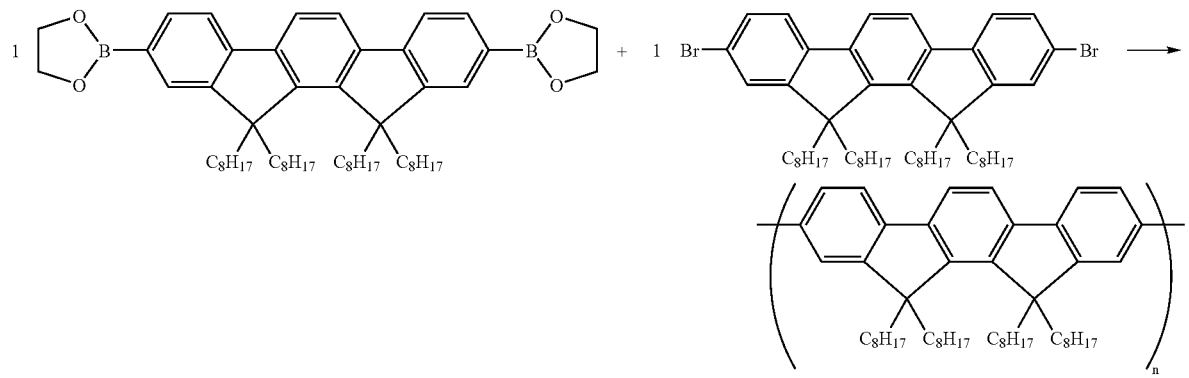
Polymer 2
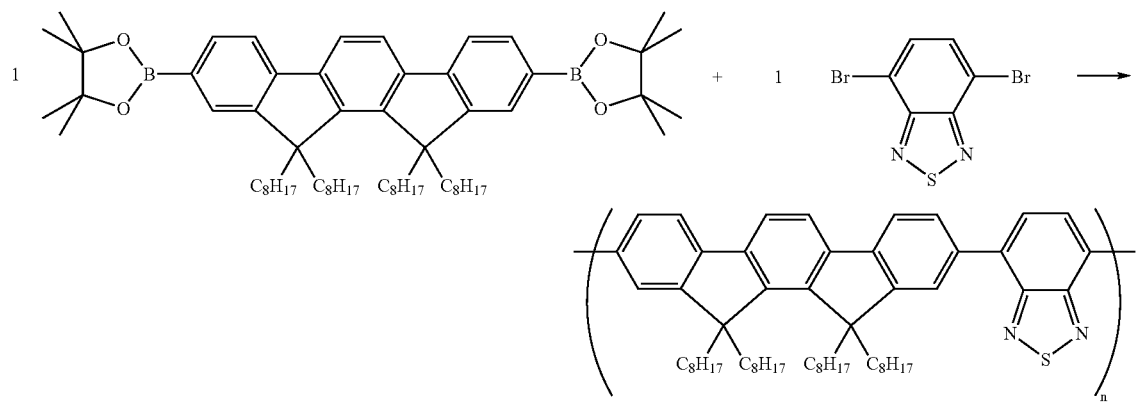
Polymer 3
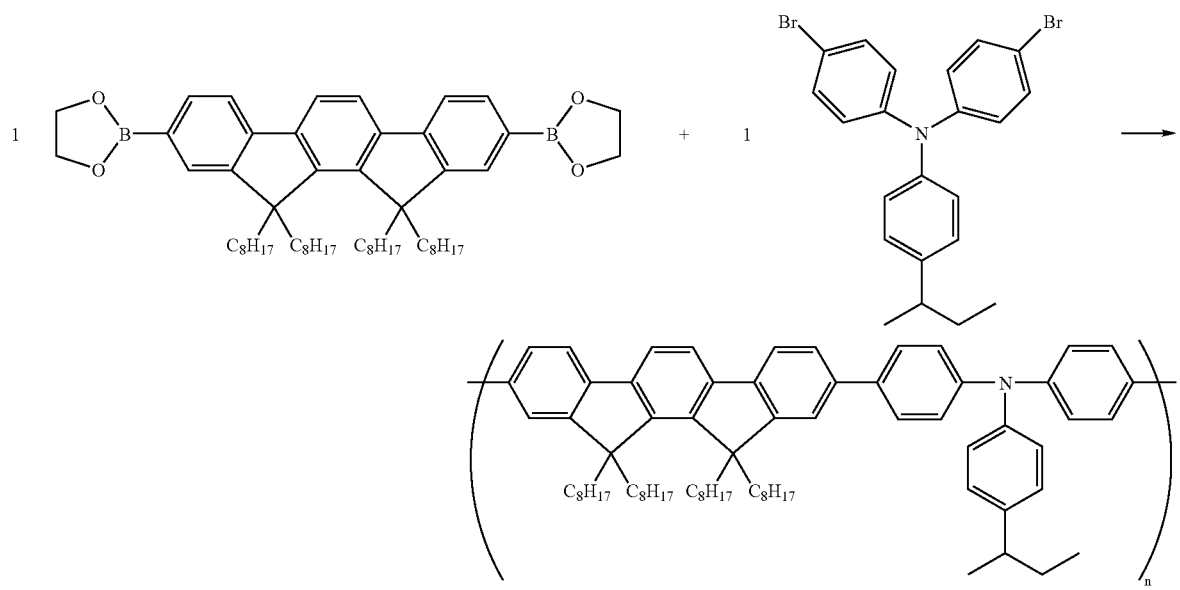
Polymer 4
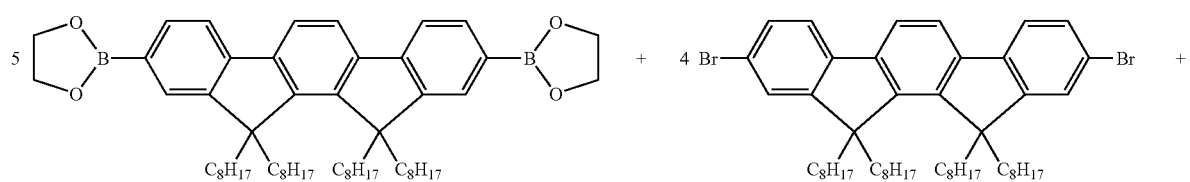

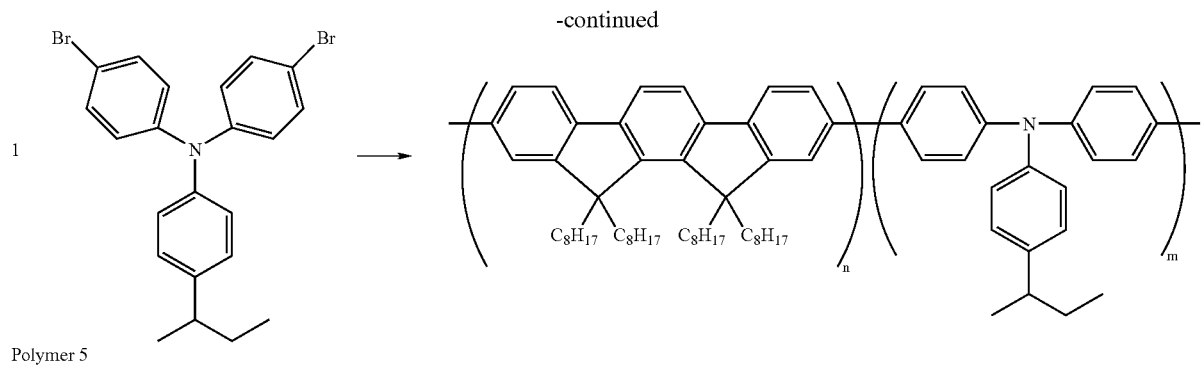
Polymer 5
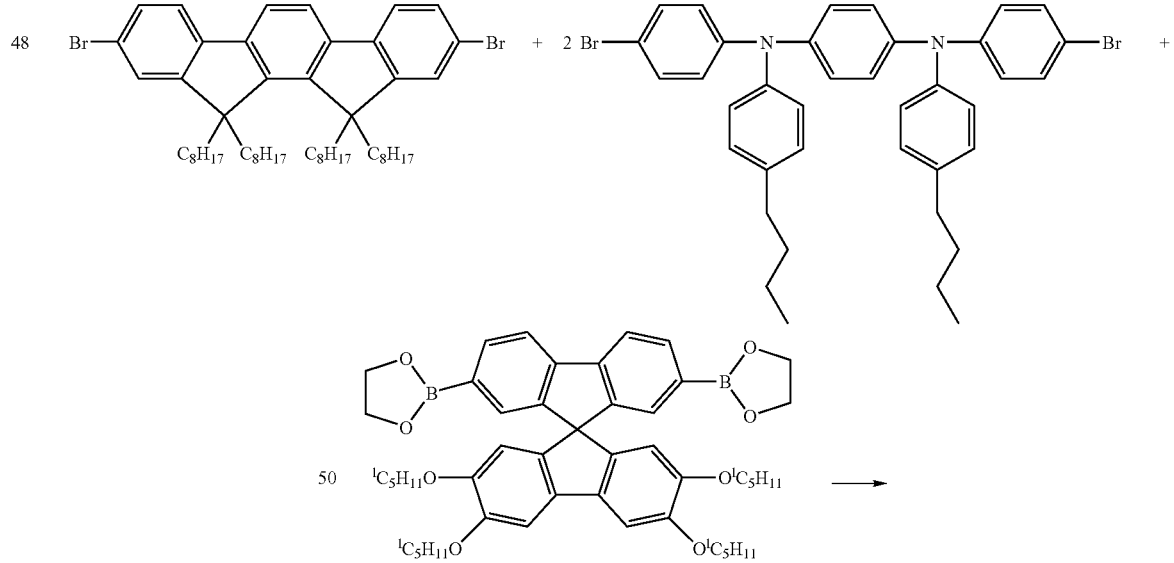
For the purpose of comparison, polymers were prepared as per polymer 5 above except that the following trans-indenofluorene monomers were used in place of the cis-indenofluorene repeat unit according to the invention:
Polymer 6
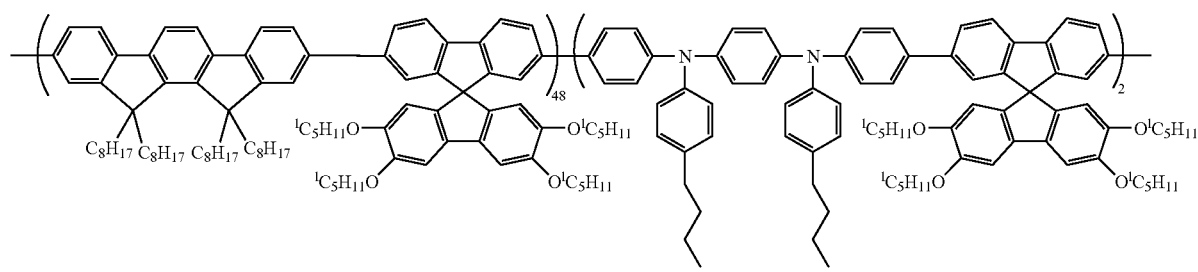
-continued
Polymer 7
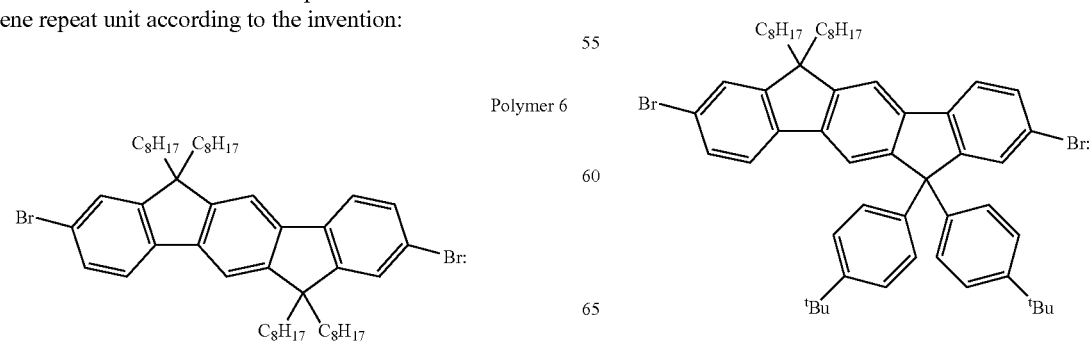

-continued

Polymer 8

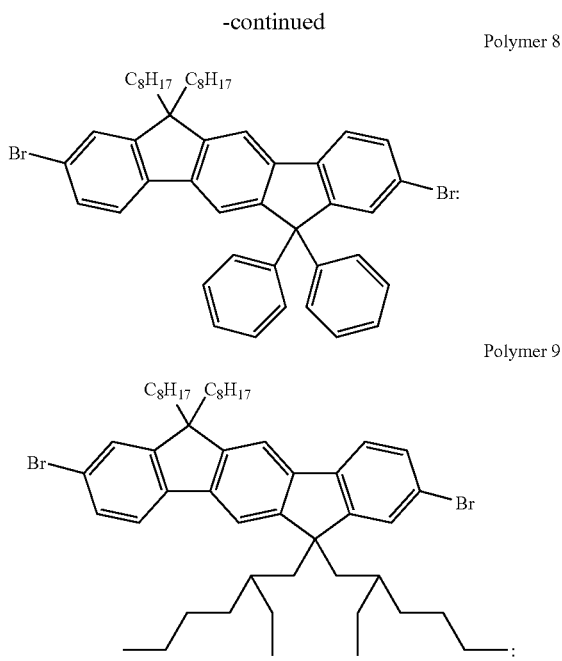

Polymer 9

Device Example

Onto indium tin oxide supported on a glass substrate (available from Applied Films, Colorado, USA) was deposited a film of poly(ethylene dioxythiophene) (PEDT/PSS), available from Bayer® as Baytron P®, by spin coating. The electroluminescent layer was formed over the layer of PEDT/PSS by spin coating from xylene solution comprising polymer 5 according to the invention. A bilayer cathode of calcium/aluminium was deposited over the electroluminescent layer and the device was encapsulated using an airtight metal enclosure containing a desiccant available from Saes Getters SpA.

For the purpose of comparison, identical devices were prepared except that comparative polymers 6, 7, 8 and 9 were used in place of polymer 5. Device performance for the devices prepared from these materials is summarised in Table 1 below.

TABLE 1

| Polymer | CIEx | CIEy | V at 100 cd/m$^2$ | Half life[1] from 800 cd/m$^2$ | Colour Shift[2] | Δ V[3] | % Burn-in[4] |
|---|---|---|---|---|---|---|---|
| 5 | 0.16 | 0.17 | 4.3 | 120 h | 0.03 | 1.0 | 3% |
| 6 | 0.17 | 0.22 | 5.7 | 140 h | 0.06 | 2.8 | 12% |
| 7 | 0.16 | 0.19 | 5.1 | 46 h | 0.04 | 0.2 | 24% |
| 8 | 0.17 | 0.23 | 5.4 | 35 h | 0.02 | 0.0 | 20% |
| 9 | 0.17 | 0.22 | 5.4 | 70 h | 0.06 | 0.6 | 1% |

[1]Half-life = time taken for luminance to fall by half at constant current.
[2]Colour shift measured at half-life and taking into account the lateral CIEx and CIEy shift from the starting colours, measured as the square root of: (CIEx colour shift)$^2$ + (CIEy colour shift)$^2$
[3]Change in drive voltage during the half life of the device.
[4]Burn-in refers to an initial fall in luminance when the device is driven followed by a more gradual decay in luminance.

As can be seen from Table 1, polymer 5 according to the invention provides the best performance across the range of parameters measured. For most parameters, polymer 5 is superior to the comparative polymers; for the remaining parameters, there is no instance where the performance of polymer 5 is significantly poorer than any of the comparative polymers.

Although the present invention has been described in terms of specific exemplary embodiments, it will be appreciated that various modifications, alterations and/or combinations of features disclosed herein will be apparent to those skilled in the art without departing from the spirit and scope of the invention as set forth in the following claims.

The invention claimed is:

1. An oligomer or polymer comprising an optionally substituted first repeat unit of formula (Ir):

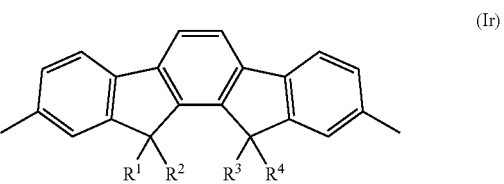

(Ir)

wherein $R^1$, $R^2$, $R^3$ and $R^4$, which may be the same or different, are independently selected from hydrogen or a substituent and two or more of $R^1$, $R^2$, $R^3$ and $R^4$ may be linked to form a ring and the oligomer or polymer comprises a second repeat unit.

2. An oligomer or polymer according to claim 1 wherein each $R^1$, $R^2$, $R^3$ and $R^4$ is independently selected from the group consisting of optionally substituted alkyl, alkoxy, aryl, or heteroaryl.

3. An oligomer or polymer according to claim 1, wherein at least one of $R^1$, $R^2$, $R^3$ and $R^4$ is optionally substituted phenyl or optionally substituted $C_{1-20}$ alkyl.

4. An oligomer or polymer according to claim 3 wherein at least one $R^1$, $R^2$, $R^3$ and $R^4$ is different from at least one other $R^1$, $R^2$, $R^3$ and $R^4$.

5. An oligomer or polymer according to claim 1, wherein the second repeat unit is selected from optionally substituted aryl, heteroaryl and triarylamine repeat units.

6. An optionally substituted monomer of formula (Im):

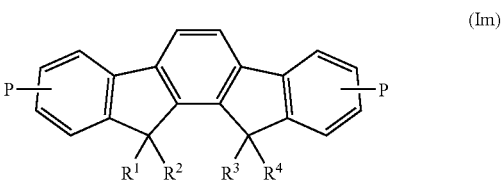

(Im)

wherein $R^1$, $R^2$, $R^3$ and $R^4$, which may be the same or different, are independently selected from hydrogen or a substituent and two or more of $R^1$, $R^2$, $R^3$ and $R^4$ may be linked to form a ring; and
each P represents a polymerisable group.

7. A monomer according to claim 6 wherein each P represents a leaving group capable of participating in a polycondensation mediated by a metal of variable oxidation state.

8. A monomer according to claim 7 wherein each P is independently selected from halogen; a moiety of formula —O—SO$_2$—Z wherein Z is selected from the group consisting of optionally substituted alkyl and aryl; or a reactive boron group selected from a boronic acid, a boronic ester or a borane.

9. A process for preparing an oligomer or polymer comprising the step of oligomerising or polymerising a monomer according to claim 6.

10. A process for preparing an oligomer or polymer according to claim 9 wherein each P is independently a halogen or a moiety of formula —O—SO$_2$—Z, and the monomer of formula (Im) is oligomerised or polymerised in the presence of a nickel complex catalyst.

11. A process for preparing a polymer according to claim 9 wherein the monomer of formula (Im) is oligomerised or polymerised with a second aromatic monomer in the presence of a palladium complex catalyst and a base and
   a. each P is the same or different and comprises a reactive boronic group and the second monomer comprises two reactive groups independently selected from halogen and a moiety of formula —O—SO$_2$—Z, or
   b. each P independently comprises a halogen or a moiety of formula —O—SO$_2$—Z and the second monomer comprises two reactive boron groups which are the same or different.

12. A process for preparing an oligomer or polymer according to claim 9, wherein one P is a reactive boron group and the other P is a halogen or a moiety of formula —O—SO$_2$—Z.

13. An optical device comprising an oligomer or polymer according to claim 1.

14. An optical device according to claim 13 wherein the oligomer or polymer is located between a first electrode for injection of charge carriers of a first type and a second electrode for injection of charge carriers of a second type.

15. A switching device comprising an oligomer or polymer according to claim 1.

16. A field effect transistor comprising an insulator having a first side and a second side; a gate electrode located on the first side of the insulator; an oligomer or polymer according to claim 1 located on the second side of the insulator; and a drain electrode and a source electrode located on the oligomer or polymer.

17. An integrated circuit comprising a field effect transistor according to claim 16.

18. A polymer comprising an optionally substituted first repeat unit of formula (Ir):

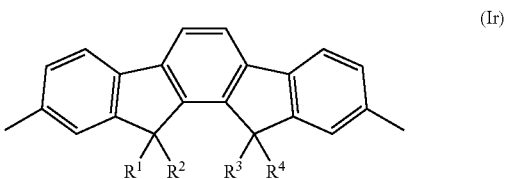

(Ir)

wherein $R^1$, $R^2$, $R^3$ and $R^4$, which may be the same or different, are independently selected from hydrogen or a substituent and two or more of $R^1$, $R^2$, $R^3$ and $R^4$ may be linked to form a ring and the oligomer or polymer comprises a second repeat unit.

* * * * *

UNITED STATES PATENT AND TRADEMARK OFFICE
CERTIFICATE OF CORRECTION

| | | |
|---|---|---|
| PATENT NO. | : 7,754,841 B2 | Page 1 of 1 |
| APPLICATION NO. | : 10/560861 | |
| DATED | : July 13, 2010 | |
| INVENTOR(S) | : Richard O'Dell et al. | |

It is certified that error appears in the above-identified patent and that said Letters Patent is hereby corrected as shown below:

In claim 12, line 1 (column 25, line 21) delete "ohgomer" and insert -- oligomer --.

In claim 18, line 7 (column 26, line 26) delete "oligomer or"

Signed and Sealed this
Fifth Day of July, 2011

David J. Kappos
*Director of the United States Patent and Trademark Office*